(12) United States Patent
Zhang et al.

(10) Patent No.: US 11,719,685 B2
(45) Date of Patent: Aug. 8, 2023

(54) SELECTION METHOD OF BASE ASPHALT FOR RUBBER ASPHALT BASED ON GREY RELATIONAL ANALYSIS

(71) Applicants: Guangxi Transportation Science and Technology Group Co., Ltd., Nanning (CN); Guangxi Jiaoke New Materials Technology Co., Ltd., Nanning (CN)

(72) Inventors: Honggang Zhang, Nanning (CN); Hua Tan, Nanning (CN); Jizong Tan, Nanning (CN); Haitao Yuan, Nanning (CN); Hongbo Zhang, Nanning (CN); Baolin Xiong, Nanning (CN); Jianping Xiong, Nanning (CN); Zehua Xie, Nanning (CN); Dongliang Kuang, Nanning (CN)

(73) Assignees: Guangxi Transportation Science and Technology Group Co., Ltd., Nanning (CN); Guangxi Jiaoke New Materials Technology Co., Ltd., Nannning (CN)

(*) Notice: Subject to any disclaimer, the term of this patent is extended or adjusted under 35 U.S.C. 154(b) by 91 days.

(21) Appl. No.: 17/546,109

(22) Filed: Dec. 9, 2021

(65) Prior Publication Data
US 2022/0187273 A1 Jun. 16, 2022

(30) Foreign Application Priority Data
Dec. 10, 2020 (CN) .......................... 202011456942.2

(51) Int. Cl.
*G01N 33/42* (2006.01)
(52) U.S. Cl.
CPC .................................. *G01N 33/42* (2013.01)

(58) Field of Classification Search
CPC ....... G01N 33/42; G01N 33/445; G01N 33/28
See application file for complete search history.

(56) References Cited

U.S. PATENT DOCUMENTS 3,940,281 A * 2/1976 Corbett .................. C10C 3/005
208/23
9,208,266 B2 * 12/2015 Kriz ....................... C10C 3/002
(Continued)

FOREIGN PATENT DOCUMENTS

| CN | 106770702 A | * | 5/2017 | ............. G01N 30/02 |
| CN | 111423736 A | * | 7/2020 | ............. C08L 95/00 |
| WO | WO-2011061662 A1 | * | 5/2011 | ............. E21B 49/00 |

*Primary Examiner* — Francis C Gray
(74) *Attorney, Agent, or Firm* — Shih IP Law Group, PLLC

(57) ABSTRACT

The present disclosure provides a selection method of base asphalt for rubber asphalt based on grey relational analysis, which belongs to the technical field of selection methods of base asphalt. The selection method includes the following steps: determining factors affecting the performance of rubber asphalt and rubber asphalt performance evaluation indicators; ranking the factors affecting the performance of rubber asphalt according to respective affecting degrees thereof on each of the rubber asphalt performance evaluation indicators by using a grey relational method; and determining affecting factors of chemical components of base asphalt to the performance of rubber asphalt, and selecting base asphalt according to the affecting factors. The present disclosure uses the grey relational analysis method to systematically study the influences of chemical components of base asphalt on the performance of rubber asphalt.

4 Claims, 1 Drawing Sheet

(56) References Cited

U.S. PATENT DOCUMENTS

| | | | |
|---|---|---|---|
| 2009/0120170 A1* | 5/2009 | Carbonell | C10G 21/003 73/61.59 |
| 2014/0180650 A1* | 6/2014 | Kriz | G06F 30/20 703/2 |
| 2015/0191598 A1* | 7/2015 | Sirota | C08L 95/00 106/273.1 |

* cited by examiner

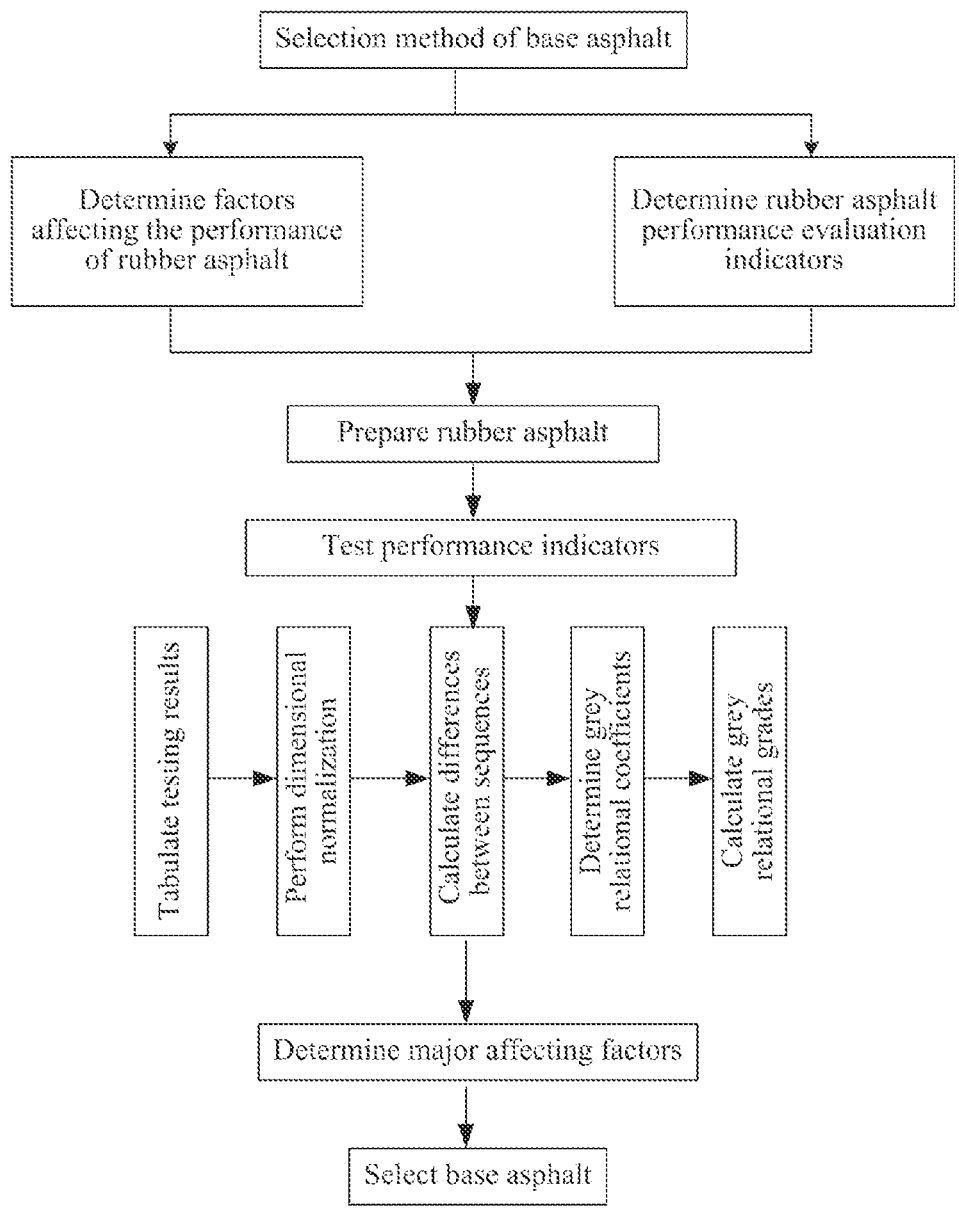

SELECTION METHOD OF BASE ASPHALT FOR RUBBER ASPHALT BASED ON GREY RELATIONAL ANALYSIS

CROSS-REFERENCE TO RELATED APPLICATIONS

This patent application claims the benefit and priority of Chinese Patent Application No. 202011456942.2, filed on Dec. 10, 2020, the disclosure of which is incorporated by reference herein in its entirety as part of the present application.

TECHNICAL FIELD

The present disclosure relates to the technical field of selection methods of base asphalt, and in particular, to a selection method of base asphalt for rubber asphalt based on grey relational analysis.

BACKGROUND ART

In recent years, rubber asphalt has been widely used at home and abroad for its performance advantages such as excellent rut resistance at high temperature and cracking resistance at low temperature, good durability, and reduction of pavement noise, as well as a series of environmentally significant advantages such as effective recycling of waste tires. At present, most studies on rubber asphalt focus on selection process, noise reduction, anti-aging performance, microscopic modification mechanism, etc. Unfortunately, little attention has been paid to the influences of chemical components of base asphalt on the performance of rubber asphalt.

Base asphalt is a major raw material of rubber asphalt, and its chemical components and technical properties directly affect the subsequent modification of asphalt and the pavement performance of rubber asphalt. The chemical components of base asphalt are closely related to an oil source and a refining process thereof, and the composition of base asphalt is complicated and is difficult to classify by elemental substances or compounds. The chemical composition and structure of base asphalt can only be characterized indirectly by gel permeation chromatography (GPC), thin layer chromatography with flame ionization detection (TLC/FID), Fourier Transform infrared spectroscopy (FTIR) and the like. During the selection of rubber asphalt, the chemical components of asphalt will have physical and chemical interactions with rubber powder particles, which may affect not only the compatibility of rubber powder with base asphalt but also the pavement performance of rubber asphalt. Therefore, the relation between the components of base asphalt and the performance of rubber asphalt is particularly complicated. Generally, comparative analysis of base asphalt and modified asphalt on molecular weight distribution, thermal decomposition temperature, and functional group change is currently adopted to indirectly study the influence of changes in asphalt components on the performance of modified asphalt. However, these methods all fail to analyze major affecting factors by statistical methods.

SUMMARY

In view of the above problems, an objective of the present disclosure is to provide a selection method of base asphalt for rubber asphalt based on grey relational analysis. The present disclosure provides a more accurate method for studying the influences of the chemical components of base asphalt on the performance of rubber asphalt and reasonably selecting base asphalt, and overcome the shortcoming of lack of systematic methods, allowing for more accurate and reasonable selection of base asphalt.

To achieve the objective of the present disclosure, the present disclosure provides the following technical solutions.

The present disclosure provides a selection method of base asphalt for rubber asphalt based on grey relational analysis, including the following steps:

determining factors affecting the performance of rubber asphalt and rubber asphalt performance evaluation indicators, where the factors affecting the performance of rubber asphalt include a saturate mass percentage, an aromatic mass percentage, a resin mass percentage, an asphaltene mass percentage, a sum of saturate and aromatic mass percentages and a sum of resin and asphaltene mass percentages in base asphalt; and the rubber asphalt performance evaluation indicators include a softening point, penetration, ductility at 5° C., viscosity at 180° C. and 48-h segregation softening point difference of rubber asphalt;

ranking the factors affecting the performance of rubber asphalt according to respective affecting degrees thereof on each of the rubber asphalt performance evaluation indicators by using a grey relational method; and determining affecting factors of chemical components of base asphalt to the performance of rubber asphalt according to the results of ranking with respect to affecting degree, and selecting base asphalt according to the affecting factors.

Preferably, the determining factors affecting the performance of rubber asphalt and rubber asphalt performance evaluation indicators may include the following steps:

selecting two or more types of alternative base asphalt to prepare rubber asphalt samples;

measuring the saturate mass percentage, the aromatic mass percentage, the resin mass percentage and the asphaltene mass percentage in each base asphalt, and calculating the sum of saturate and aromatic mass percentages and the sum of resin and asphaltene mass percentages in each base asphalt; and testing the rubber asphalt samples with respect to the softening point, the penetration, the ductility at 5° C., the viscosity at 180° C. and the 48-h segregation softening point difference.

Preferably, the ranking the factors affecting the performance of rubber asphalt according to respective affecting degrees thereof on each of the rubber asphalt performance evaluation indicators by using a grey relational method may include the following steps:

calculating grey relational grades: calculating respective grey relational coefficients of the factors affecting the performance of rubber asphalt to the rubber asphalt performance evaluation indicators by using the grey relational method; calculating respective averages of the grey relational coefficients to obtain respective grey relational grades of the factors affecting the performance of rubber asphalt to the rubber asphalt performance evaluation indicators; and ranking the chemical components of base asphalt according to respective affecting degrees thereof on each performance indicator of rubber asphalt based on the values of the grey relational grades of the factors affecting the performance of rubber asphalt to the rubber asphalt performance evaluation indicators.

Preferably, the calculating grey relational grades may include the following steps:

tabulating testing results: using each of the softening point, the penetration, the ductility at 5° C., the viscosity at 180° C. and the 48-h segregation softening point difference of rubber asphalt as a reference variable, which is expressed as the following discrete sequence:

$$X_0=(X_0(k)|k=1,2,\ldots,n); n\geq 2; \quad \text{Reference variable}$$

where the reference variable $X_0$ represents a set of values on a rubber asphalt performance evaluation indicator obtained from the n types of rubber asphalt;

using the factors affecting the performance of rubber asphalt as comparative variables, each of which is expressed as the following discrete sequence:

$$X_i=(X_i(k)|k=1,2,\ldots 6)\ (i=1,2,\ldots,n); n\geq 2; \quad \text{Comparative variable}$$

where the comparative variable $X_i$ represents a set of values of each factor affecting the performance of rubber asphalt as a variable, with i representing the ith component variable and k representing the kth base asphalt;

tabulating the comparative variables and the reference variable, with different variables being arranged in rows and different samples being arranged in columns;

performing dimensional normalization: performing dimensional normalization on different variables by dividing each value by an average to obtain respective values of the reference variable and the comparative variables, which are calculated according to Formula (1) below:

$$\begin{cases} Y_0 = \{X_0(k)/\overline{X}_0 \mid k = 1, 2, \ldots 6\} \\ Y_i\{X_i(k)/\overline{X}_i \mid k = 1, 2, \ldots, 6\}(i = 1, 2, \ldots, 6) \end{cases} \quad \text{Formula (1);}$$

where $k = 1, 2, \ldots\ldots, n; n \geq 2$;

$Y_0$ represents a set obtained by dividing each value in $X_0$ by an average of all the values in $X_0$, and $Y_i$ represents a set obtained by dividing each value in $X_i$ by an average of all the values in $X_i$;

calculating differences between sequences: after the dimensional normalization, calculating differences between the values of the reference variable row and each comparative variable row in corresponding columns according to the following Formula (2), and obtaining the absolute values of the differences to form a new table with the reference variable row omitted:

$$\Delta_i(k)=|Y_0(k)-Y_i(k)| \quad \text{Formula (2);}$$

where $\Delta_i(k)$ represents the absolute value;

determining grey relational coefficients: calculating relational coefficients of comparative sequences to the reference sequence according to Formula (3) below:

$$\xi_i = \frac{\min\limits_{i=1,n}\left[\min\limits_{k=1,n}\Delta_i(k)\right] + \rho\max\limits_{i=1,n}\left[\max\limits_{k=1,n}\Delta_i(k)\right]}{\Delta_i(k) + \rho\max\limits_{i=1,n}\left[\max\limits_{k=1,n}\Delta_i(k)\right]}; \quad \text{Formula (3)}$$

where $\rho$ is an identification coefficient, generally $\rho \in (0, 1)$, having a value of 0.5; and $$\min\limits_{i}\left[\min\limits_{k}\Delta_i(k)\right]$$

represents a minimum difference of two extremes, while $$\min\limits_{i}\left[\min\limits_{k}\Delta_i(k)\right]$$

represents a maximum difference of two extremes;

calculating grey relational grade according to Formula (4) below:

$$r_i = \frac{1}{n}\sum \xi_i(k); \quad \text{Formula (4)}$$

and calculating respective averages of the relational coefficients to obtain the grey relational grades.

The present disclosure provides a selection method of base asphalt for rubber asphalt based on grey relational analysis, including the following steps: determining factors affecting the performance of rubber asphalt and rubber asphalt performance evaluation indicators, where the factors affecting the performance of rubber asphalt include a saturate mass percentage, an aromatic mass percentage, a resin mass percentage, an asphaltene mass percentage, a sum of saturate and aromatic mass percentages and a sum of resin and asphaltene mass percentages in base asphalt; and the rubber asphalt performance evaluation indicators include a softening point, penetration, ductility at 5° C., viscosity at 180° C. and 48-h segregation softening point difference of rubber asphalt; ranking the factors affecting the performance of rubber asphalt according to respective affecting degrees thereof on each of the rubber asphalt performance evaluation indicators by using a grey relational method; and determining affecting factors of chemical components of base asphalt to the performance of rubber asphalt according to the results of ranking with respect to affecting degree, and selecting base asphalt according to the affecting factors. The present disclosure uses the grey relational analysis method to systematically study the influences of chemical components of base asphalt on the performance of rubber asphalt.

Compared with the prior art, the present disclosure has the following advantages:

1. Due to the use of a plurality of parameters and comprehensive selection of performance indicators of rubber asphalt, the results obtained can accurately reflect the ranking of the factors affecting the performance of rubber asphalt.

2. The method of the present disclosure has the advantages of convenient operation, few restrictions, easy implementation, and reliable results, and is worthy of practical application and promotion.

BRIEF DESCRIPTION OF THE DRAWINGS

FIG. 1 is a flowchart of a selection method of base asphalt for rubber asphalt based on grey relational analysis according to the present disclosure.

DETAILED DESCRIPTION OF THE EMBODIMENTS

The present disclosure provides a selection method of base asphalt for rubber asphalt based on grey relational analysis, including the following steps:

determine factors affecting the performance of rubber asphalt and rubber asphalt performance evaluation indicators, where the factors affecting the performance of rubber asphalt include a saturate mass percentage, an aromatic mass percentage, a resin mass percentage, an asphaltene mass percentage, a sum of saturate and aromatic mass percentages and a sum of resin and asphaltene mass percentages in base asphalt; and the rubber asphalt performance evaluation indicators include a softening point, penetration, ductility at 5° C., viscosity at 180° C. and 48-h segregation softening point difference of rubber asphalt;

rank the factors affecting the performance of rubber asphalt according to respective affecting degrees thereof on each of the rubber asphalt performance evaluation indicators by using a grey relational method; and determine affecting factors of chemical components of base asphalt to the performance of rubber asphalt according to the results of ranking with respect to affecting degree, and select base asphalt according to the affecting factors.

In the present disclosure, the process of determining factors affecting the performance of rubber asphalt and rubber asphalt performance evaluation indicators preferably includes the following steps:

select two or more types of alternative base asphalt to prepare rubber asphalt samples;

measure the saturate mass percentage, the aromatic mass percentage, the resin mass percentage and the asphaltene mass percentage in each base asphalt, and calculate the sum of saturate and aromatic mass percentages and the sum of resin and asphaltene mass percentages in each base asphalt; and test the rubber asphalt samples with respect to the softening point, the penetration, the ductility at 5° C., the viscosity at 180° C. and the 48-h segregation softening point difference.

In the present disclosure, it is more preferred to select 6 types of alternative base asphalt.

In a specific example of the present disclosure, the preparation of rubber asphalt samples preferably includes the following steps: select 6 different types of alternative base asphalt to prepare 6 rubber asphalt samples: sample A, sample B, sample C, sample D, sample E, and sample F.

In the present disclosure, the process of ranking the factors affecting the performance of rubber asphalt according to respective affecting degrees thereof on each of the rubber asphalt performance evaluation indicators by using a grey relational method preferably includes the following steps:

calculate grey relational grades: calculate respective grey relational coefficients of the factors affecting the performance of rubber asphalt to the rubber asphalt performance evaluation indicators by using the grey relational method; calculate respective averages of the grey relational coefficients to obtain respective grey relational grades of the factors affecting the performance of rubber asphalt to the rubber asphalt performance evaluation indicators; and rank the chemical components of base asphalt according to respective affecting degrees thereof on each performance indicator of rubber asphalt based on the values of the grey relational grades of the factors affecting the performance of rubber asphalt to the rubber asphalt performance evaluation indicators.

In the present disclosure, the process of calculating grey relational grades preferably includes the following steps:

tabulate testing results: use each of the softening point, the penetration, the ductility at 5° C., the viscosity at 180° C. and the 48-h segregation softening point difference of rubber asphalt as a reference variable, and express the reference variable as the following discrete sequence:

$$X_0=(X_0(k)|k=1,2,\ldots n); n\geq 2;\quad \text{Reference variable}$$

where the reference variable $X_0$ represents a set of values on a rubber asphalt performance evaluation indicator obtained from the n types of rubber asphalt;

use the factors affecting the performance of rubber asphalt as comparative variables, and express each comparative variable as the following discrete sequence:

$$X_i=(X_i(k)|k=1,2,\ldots,6)\ (i=1,2,\ldots,n); n\geq 2;\quad \text{Comparative variable}$$

where the comparative variable $X_i$ represents a set of values of each factor affecting the performance of rubber asphalt as a variable, with i representing the ith component variable and k representing the kth base asphalt;

tabulate the comparative variables and the reference variable, with different variables being arranged in rows and different samples being arranged in columns;

perform dimensional normalization: perform dimensional normalization on different variables by dividing each value by an average to obtain respective values of the reference variable and the comparative variables, and calculate such values according to Formula (1) below:

$$\begin{cases} Y_0 = \{X_0(k)/\overline{X}_0 \mid k = 1, 2, \ldots 6\} \\ Y_i\{X_i(k)/\overline{X}_i \mid k = 1, 2, \ldots, 6\}(i = 1, 2, \ldots, 6) \end{cases} \quad \text{Formula (1);}$$

where $k = 1, 2, \ldots \ldots, n; n \geq 2;$ $Y_0$ represents a set obtained by dividing each value in $X_0$ by an average of all the values in $X_0$, and $Y_i$ represents a set obtained by dividing each value in $X_i$ by an average of all the values in $X_i$;

calculate differences between sequences: after the dimensional normalization, calculate differences between the values of the reference variable row and each comparative variable row in corresponding columns according to the following Formula (2), and obtain the absolute values of the differences to form a new table with the reference variable row omitted:

$$\Delta_i(k)=|Y_0(k)-Y_i(k)|\quad \text{Formula (2);}$$

where $\Delta_i(k)$ represents the absolute value;

determine grey relational coefficients: calculate relational coefficients of comparative sequences to the reference sequence according to Formula (3) below:

$$\xi_i = \frac{\min\limits_{i=1,n}\left[\min\limits_{k=1,n}\Delta_i(k)\right] + \rho\max\limits_{i=1,n}\left[\max\limits_{k=1,n}\Delta_i(k)\right]}{\Delta_i(k) + \rho\max\limits_{i=1,n}\left[\max\limits_{k=1,n}\Delta_i(k)\right]}; \quad \text{Formula (3)}$$

where ρ is an identification coefficient, generally $\rho\in(0, 1)$, having a value of 0.5; and $$\min\limits_{i}\left[\min\limits_{k}\Delta_i(k)\right]$$

represents a minimum difference of two extremes, while $$\min_{i}\left[\min_{k}\Delta_{i}(k)\right]$$

represents a maximum difference of two extremes;
calculate a grey relational grade according to Formula (4) below:

$$r_i = \frac{1}{n}\sum \xi_i(k);\qquad \text{Formula (4)}$$

and
calculate respective averages of the relational coefficients to obtain the grey relational grades.

In the present disclosure, the reference variable $X_0$ represents a set of values on a performance indicator obtained from 6 types of rubber asphalt. Taking the softening point of rubber asphalt for example, the reference variable $X_0$ represents a set of softening point values of 6 types of rubber asphalt, and there are a total of 6 values included in $X_0$: $X_0$ (1), $X_0$ (2), $X_0$ (3), $X_0$ (4), $X_0$ (5), and $X_0$ (6), with $X_0$ (1) representing the softening point of the first rubber asphalt (sample A), and so on.

In the present disclosure, the comparative variable $X_i$ represents a set of values on a component variable obtained from 6 types of rubber asphalt, with i representing the ith component variable and k representing the kth base asphalt. For example, $X_i$ represents a set of saturate mass percentage values of 6 types of base asphalt, including a total of 6 values: $X_1$ (1), $X_1$ (2), $X_1$ (3), $X_1$ (4), $X_1$ (5), and $X_1$ (6), with $X_1$ (3) representing the saturate mass percentage in the third base asphalt, and so on. Similarly, $X_3$ (4) represents the asphaltene mass percentage in the fourth base asphalt.

To further explain the present disclosure, the selection method for base asphalt for rubber asphalt based on grey relational analysis provided in the present disclosure will be described in detail in conjunction with examples, which, however, cannot be interpreted as limitations to the protection scope of the present disclosure.

FIG. 1 is a flowchart of the selection method for base asphalt for rubber asphalt based on grey relational analysis according to Example 1 of the present disclosure. The selection method includes the following steps: determine factors affecting the performance of rubber asphalt and rubber asphalt performance evaluation indicators; rank the factors affecting the performance of rubber asphalt according to respective affecting degrees thereof on each of the rubber asphalt performance evaluation indicators by using a grey relational method, in which the preparation of rubber asphalt and testing of performance indicators are involved; determine affecting factors of chemical components of base asphalt to the performance of rubber asphalt, and select base asphalt according to the affecting factors. The process of testing the performance indicators includes tabulation of testing results, dimensional normalization, calculation of differences between sequences, calculation of grey relational coefficients, and calculation of grey relational grades.

Example 1

A selection method of base asphalt for rubber asphalt based on grey relational analysis was implemented by the following steps:

1) A plurality of factors affecting the performance of rubber asphalt and a plurality of rubber asphalt performance evaluation indicators were determined.

In this example, a saturate mass percentage, an aromatic mass percentage, a resin mass percentage, an asphaltene mass percentage, a sum of saturate and aromatic mass percentages and a sum of resin and asphaltene mass percentages in base asphalt were selected as 6 factors affecting the performance of rubber asphalt.

The softening point, penetration, ductility at 5° C., viscosity at 180° C. and 48-h segregation softening point difference of rubber asphalt were selected as the rubber asphalt performance evaluation indicators.

2) The affecting factors of chemical components of base asphalt to the performance of rubber asphalt were ranked according to their affecting degrees by using the grey relational method:

2.1) Preparation of rubber asphalt: Gaofu 70# base asphalt, Maoming 70# base asphalt, Shell 70# base asphalt, Esso 70# base asphalt, Dongyou 70# base asphalt and Tipco 70# base asphalt, and 30-mesh rubber powder (rubber powder was doped in an amount of 25% by mass of asphalt) were selected to prepare 6 different types of rubber asphalt: sample A, sample B, sample C, sample D, sample E and sample F.

2.2) Testing on affecting factors: the saturate, aromatic, resin and asphaltene components of the 6 types of base asphalt were tested, and the sum of the saturate and aromatic mass percentages and the sum of resin and asphaltene mass percentages in each of the 6 types of base asphalt were calculated, with results being listed in Table 1.

TABLE 1

Testing Results (wt %) of Four Components of Base Asphalt

| Asphalt Brand | Saturate (%) | Aromatic (%) | Resin (%) | Asphaltene (%) | Resin + Asphaltene (%) | Saturate + Aromatic (%) |
|---|---|---|---|---|---|---|
| Gaofu 70# | 18.36 | 46.82 | 26.62 | 8.20 | 34.82 | 65.18 |
| Maoming 70# | 14.56 | 41.36 | 31.52 | 12.56 | 44.08 | 55.92 |
| Shell 70# | 14.19 | 43.75 | 31.73 | 10.33 | 42.06 | 57.94 |
| Esso 70# | 17.33 | 45.06 | 28.55 | 9.06 | 37.61 | 62.39 |
| Dongyou 70# | 13.20 | 43.24 | 30.23 | 13.33 | 43.56 | 56.44 |
| Tipco 70# | 17.24 | 46.30 | 27.22 | 9.24 | 36.46 | 63.54 |

2.3: Testing on performance indicators of rubber asphalt: with reference to Standard Test Methods of Bitumen and Bituminous Mixtures for Highway Engineering (JTG. E20-2011), the softening point, penetration, ductility at 5° C., viscosity at 180° C. and 48-h segregation softening point difference of each sample were tested, with results being listed in Table 2.

TABLE 2

Performance Testing Results of Rubber Asphalt

| | Softening Point (° C.) | Penetration (0.1 mm) | Ductility at 5° C. (cm) | Viscosity at 180° C. (Pa · s) | 48-h Segregation Softening Point Difference (° C.) |
|---|---|---|---|---|---|
| Sample A | 61.6 | 46.5 | 15.3 | 1.65 | 1.6 |
| Sample B | 70.3 | 45.0 | 9.8 | 2.29 | 2.2 |
| Sample C | 70.5 | 43.5 | 10.5 | 1.96 | 0.9 |
| Sample D | 62.7 | 46.6 | 11.6 | 2.03 | 1.6 |
| Sample E | 70.0 | 40.1 | 9.0 | 2.35 | 1.9 |
| Sample F | 61.6 | 48.0 | 10.9 | 1.99 | 1.4 |

2.4) Calculation of grey relational grades: the grey relational method was used to analyze the influences of the chemical components of base asphalt on the performance of rubber asphalt, including the steps of tabulation of testing results, dimensional normalization, calculation of differences between sequences, calculation of grey relational coefficients, calculation of grey relational grades, and ranking. Taking the calculation process of grey relational grades of the affecting factors to the softening point of rubber asphalt for example, the specific steps were as follows:

(1) Tabulation of testing results: the softening point values of different types of rubber asphalt were arranged in a row as a reference sequence Xa, and respective percentages of four components of asphalt (listed as a group of indicators), and the sum of resin and asphaltene percentages and the sum of saturate and aromatic percentages are arranged in different rows to form comparative sequences: $X_1$ (saturate, wt %), $X_2$ (aromatic, wt %), $X_3$ (resin, wt %), $X_4$ (asphaltene, wt %), $X_5$ (the sum of resin and asphaltene percentages, wt %), $X_6$ (the sum of saturate and aromatic percentages, wt %), with the results being shown in Table 3.

TABLE 3

Testing Results of Softening Point of Rubber Asphalt and Four Components of Base Asphalt

| | Gaofu | Maoming | Esso | Shell | Dongyou | Tipco |
|---|---|---|---|---|---|---|
| Softening point | 61.6 | 70.3 | 62.7 | 70.5 | 70 | 61.6 |
| Saturate | 18.36 | 14.56 | 17.33 | 14.19 | 13.2 | 17.24 |
| Aromatic | 46.82 | 41.36 | 45.06 | 43.75 | 43.24 | 46.3 |
| Resin | 26.62 | 31.52 | 28.55 | 31.73 | 30.23 | 27.22 |
| Asphaltene | 8.2 | 12.56 | 9.06 | 10.33 | 13.33 | 9.24 |
| Resin + Asphaltene | 34.82 | 44.08 | 37.61 | 42.06 | 43.56 | 36.46 |
| Saturate + Aromatic | 65.18 | 55.92 | 62.39 | 57.94 | 56.44 | 63.54 |

(2) Dimensional normalization: dimensional normalization was performed on different variables by dividing each value by an average. The calculation was performed according to Formula (1), with the calculation results being shown in Table 4.

TABLE 4

Initialization of Testing Results

| Affecting Factor | Gaofu | Maoming | Esso | Shell | Dongyou | Tipco |
|---|---|---|---|---|---|---|
| $Y_0$ | 0.932 | 1.063 | 0.948 | 1.066 | 1.059 | 0.932 |
| $Y_1$ | 1.161 | 0.921 | 1.096 | 0.897 | 0.835 | 1.090 |

TABLE 4-continued

Initialization of Testing Results

| Affecting Factor | Gaofu | Maoming | Esso | Shell | Dongyou | Tipco |
|---|---|---|---|---|---|---|
| $Y_2$ | 1.054 | 0.931 | 1.014 | 0.985 | 0.973 | 1.042 |
| $Y_3$ | 0.908 | 1.075 | 0.974 | 1.083 | 1.031 | 0.929 |
| $Y_4$ | 0.779 | 1.192 | 0.860 | 0.981 | 1.266 | 0.877 |
| $Y_5$ | 0.922 | 1.167 | 0.996 | 1.114 | 1.153 | 0.965 |
| $Y_6$ | 1.082 | 0.928 | 1.036 | 0.962 | 0.937 | 1.055 |

(3) Calculation of differences between sequences: after the dimensional normalization, differences between the values of the variable row and each comparative variable row in corresponding columns (without considering the reference variable row) were calculated and the absolute values of the differences were obtained. The calculation was performed according to Formula (2) to obtain the absolute differences between the normalized sequence of each affecting factor and the normalized sequence of the softening point of rubber asphalt, with the calculation results being shown in Table 5.

TABLE 5

Absolute Differences of Sequences of Different Affecting Factors

| Absolute Difference | Gaofu | Maoming | Esso | Shell | Dongyou | Tipco |
|---|---|---|---|---|---|---|
| $\Delta_{01}$ | 0.229 | 0.143 | 0.148 | 0.169 | 0.224 | 0.159 |
| $\Delta_{02}$ | 0.122 | 0.132 | 0.066 | 0.081 | 0.085 | 0.111 |
| $\Delta_{03}$ | 0.024 | 0.012 | 0.026 | 0.016 | 0.027 | 0.003 |
| $\Delta_{04}$ | 0.153 | 0.129 | 0.088 | 0.086 | 0.207 | 0.054 |
| $\Delta_{05}$ | 0.010 | 0.104 | 0.048 | 0.047 | 0.095 | 0.034 |
| $\Delta_{06}$ | 0.150 | 0.135 | 0.087 | 0.104 | 0.122 | 0.123 |

(4) Determination of grey relational coefficients: from Table 5, it could be obtained that $$\Delta_{max} = \max_i \max_k |X_0(k) - X_i(k)| = 0.229 \text{ and } \Delta_{min} = \min_i \min_k |X_0(k) - X_i(k)| = 0.003.$$

The relational coefficient of each value was calculated according to Formula (3) (ρ=0.5), with the calculation results being shown in Table 6.

TABLE 6

Grey Relational Coefficients of Different Affecting Factors

| Relational Coefficient | Gaofu | Maoming | Esso | Shell | Dongyou | Tipco | Relational Grade |
|---|---|---|---|---|---|---|---|
| $\zeta_{01}$ | 0.342 | 0.458 | 0.449 | 0.415 | 0.348 | 0.431 | 0.407 |
| $\zeta_{02}$ | 0.497 | 0.477 | 0.651 | 0.600 | 0.589 | 0.523 | 0.556 |
| $\zeta_{03}$ | 0.852 | 0.929 | 0.839 | 0.899 | 0.829 | 1.000 | 0.869 |
| $\zeta_{04}$ | 0.440 | 0.483 | 0.580 | 0.588 | 0.366 | 0.696 | 0.525 |
| $\zeta_{05}$ | 0.947 | 0.538 | 0.726 | 0.726 | 0.562 | 0.793 | 0.715 |
| $\zeta_{06}$ | 0.444 | 0.472 | 0.582 | 0.537 | 0.498 | 0.495 | 0.505 |

(5) Calculation of grey relational grades: the grey relational grade between two sequences was calculated according to Formula (4), with the calculation results being shown in Table 6.

Each of the penetration, ductility, viscosity and 48-h segregation softening point difference of rubber asphalt was used as the reference variable, while respective percentages of four components of asphalt (listed as a group of indicators), and the sum of resin and asphaltene percentages and the sum of saturate and aromatic percentages were used as the comparative variables. The steps of (1) tabulation of testing results, (2) dimensional normalization, (3) calculation of differences between sequences, (4) determination of grey relational coefficients and (5) calculation of grey relational grades in the calculation of relational grades were performed repeatedly to obtain the relational grades of the affecting factors to the penetration ductility, viscosity and 48-h segregation softening point difference of rubber asphalt, respectively, with the calculation results being shown in Table 7.

(2) Ranking of the affecting factors with respect to the influence on the penetration of rubber asphalt As could be seen from Table 7, the affecting factors were ranked according to their affecting degrees on the penetration of rubber asphalt in the following order: the sum of saturate and aromatic mass percentages>the aromatic mass percentage>the saturate mass percentage>the resin mass percentage>the sum of resin and asphaltene mass percentages>the asphaltene mass percentage.

(3) Ranking of the affecting factors with respect to the influence on the ductility at 5° C. of rubber asphalt As could be seen from Table 7, the affecting factors were ranked according to their affecting degrees on the ductility at 5° C. of rubber asphalt in the following order: the saturate mass percentage>the sum of saturate and aromatic mass percentages>the aromatic mass percentage>the resin mass percentage>the sum of resin and asphaltene mass percentages>the asphaltene mass percentage.

TABLE 7

Summarization of Relational Grade Values of Different Sequences

| Relational Grade r | Saturate | Aromatic | Resin | Asphaltene | Resin + Asphaltene | Saturate + Aromatic |
|---|---|---|---|---|---|---|
| Softening point | 0.407 | 0.556 | 0.869 | 0.525 | 0.715 | 0.505 |
| Penetration | 0.748 | 0.844 | 0.647 | 0.536 | 0.601 | 0.877 |
| Ductility | 0.794 | 0.761 | 0.653 | 0.576 | 0.625 | 0.793 |
| Viscosity | 0.534 | 0.660 | 0.735 | 0.724 | 0.785 | 0.645 |
| Segregation softening point difference | 0.538 | 0.635 | 0.672 | 0.673 | 0.680 | 0.604 |

2.5) The affecting factors were ranked according to their affecting degrees on the pavement performance of rubber asphalt. Based on the values of the grey relational grades of 6 affecting factors to the pavement performance of rubber asphalt, the affecting factors were ranked according to their affecting degrees on the pavement performance. When the grey relational grade of a factor was closer to 1, the factor had greater influence on the system.

(1) Ranking of the affecting factors with respect to the influence on the softening point of rubber asphalt As could be seen from the Table 7, the affecting factors were ranked according to their affecting degrees on the softening point of rubber asphalt in the following order: the resin mass percentage>the sum of resin and asphaltene mass percentages>the aromatic mass percentage>the asphaltene mass percentage>the sum of saturate and aromatic mass percentages>the saturate mass percentage.

(4) Ranking of the affecting factors with respect to the influence on the viscosity at 180° C. of rubber asphalt As could be seen from Table 7, the affecting factors were ranked according to their affecting degrees on the viscosity at 180° C. of rubber asphalt in the following order: the sum of resin and asphaltene mass percentages>the resin mass percentage>the asphaltene mass percentage>the aromatic mass percentage>the sum of saturate and aromatic mass percentages>the saturate mass percentage.

(5) Ranking of the affecting factors with respect to the influence on the 48-h segregation softening point difference of rubber asphalt As could be seen from Table 7, the affecting factors were ranked according to their affecting degrees on the 48-h segregation softening point difference of rubber asphalt in the following order: the sum of resin and asphaltene mass percentages>the asphaltene mass percentage>the resin mass percentage>the aromatic mass percentage>the sum of saturate and aromatic mass percentages>the saturate mass percentage.

3) Major affecting factors of the chemical components of base asphalt to the performance of rubber asphalt were determined:

By step 2.5), the major affecting factors of the chemical components of base asphalt to the performance of rubber asphalt could be obtained, where the resin mass percentage showed the highest affecting degree on the softening point of rubber asphalt; the sum of saturate and aromatic mass percentages showed the highest affecting degree on the penetration of rubber asphalt; the saturate mass percentage showed the highest affecting degree on the ductility at 5° C. of rubber asphalt; the sum of resin and asphaltene mass percentages showed the highest affecting degree on the viscosity at 180° C. and the 48-h segregation softening point difference of rubber asphalt.

By analyzing the influences of the percentages of four components in base asphalt on the pavement performance of rubber asphalt, the present disclosure can provide some theoretical references for the production, application and promotion of rubber asphalt. In view of different requirements of different application areas and different pavement structure layers on the pavement performance of rubber asphalt, base asphalt can be selected or rubber asphalt can be further regulated and modified based on the above conclusions. For example, as regards rubber asphalt requiring high performance at high temperature, it is desirable to select base asphalt having a high percentage of resin as the raw material, and for rubber asphalt requiring high performance at low temperature, it is desirable to select base asphalt having a high total percentage of resin and asphaltene as the raw material. After base asphalt is selected, the components of the base asphalt can be regulated by adding desired components.

The foregoing are merely descriptions of preferred embodiments of the present disclosure, and are not intended to limit the present disclosure in any form. It should be noted that improvements and modifications can be made by a person of ordinary skill in the art without departing from the principles of the present disclosure, and these improvements and modifications shall be deemed as falling within the protection scope of the present disclosure.

What is claimed is:

1. A selection method of base asphalt for rubber asphalt based on grey relational analysis, comprising the following steps:
    determining factors affecting the performance of rubber asphalt and rubber asphalt performance evaluation indicators, wherein the factors affecting the performance of rubber asphalt comprise a saturate mass percentage, an aromatic mass percentage, a resin mass percentage, an asphaltene mass percentage, a sum of saturate and aromatic mass percentages and a sum of resin and asphaltene mass percentages in base asphalt; and the rubber asphalt performance evaluation indicators comprise a softening point, penetration, ductility at 5° C., viscosity at 180° C. and 48-h segregation softening point difference of rubber asphalt;
    ranking the factors affecting the performance of rubber asphalt according to respective affecting degrees thereof on each of the rubber asphalt performance evaluation indicators by using a grey relational method; and
    determining affecting factors of chemical components of base asphalt to the performance of rubber asphalt according to the results of ranking with respect to affecting degree, and selecting base asphalt according to the affecting factors.

2. The selection method according to claim 1, wherein the determining factors affecting the performance of rubber asphalt and rubber asphalt performance evaluation indicators comprises the following steps:
    selecting two or more types of alternative base asphalt to prepare rubber asphalt samples;
    measuring the saturate mass percentage, the aromatic mass percentage, the resin mass percentage and the asphaltene mass percentage in each base asphalt, and calculating the sum of saturate and aromatic mass percentages and the sum of resin and asphaltene mass percentages in each base asphalt; and
    testing the rubber asphalt samples with respect to the softening point, the penetration, the ductility at 5° C., the viscosity at 180° C. and the 48-h segregation softening point difference.

3. The selection method according to claim 2, wherein the ranking the factors affecting the performance of rubber asphalt according to respective affecting degrees thereof on each of the rubber asphalt performance evaluation indicators by using a grey relational method comprises the following steps:
    calculating grey relational grades: calculating respective grey relational coefficients of the factors affecting the performance of rubber asphalt to the rubber asphalt performance evaluation indicators by using the grey relational method; calculating respective averages of the grey relational coefficients to obtain respective grey relational grades of the factors affecting the performance of rubber asphalt to the rubber asphalt performance evaluation indicators; and
    ranking the chemical components of base asphalt according to respective affecting degrees thereof on each performance indicator of rubber asphalt based on the values of the grey relational grades of the factors affecting the performance of rubber asphalt to the rubber asphalt performance evaluation indicators.

4. The selection method according to claim 3, wherein the calculating grey relational grades comprises the following steps:
    tabulating testing results: using each of the softening point, the penetration, the ductility at 5° C., the viscosity at 180° C. and the 48-h segregation softening point difference of rubber asphalt as a reference variable, which is expressed as the following discrete sequence:

$X_0=(X_0(k)|k=1,2,\ldots,n); n \geq 2;$      reference variable wherein the reference variable $X_0$ represents a set of values on a rubber asphalt performance evaluation indicator obtained from the n types of rubber asphalt;
    using the factors affecting the performance of rubber asphalt as comparative variables, each of which is expressed as the following discrete sequence:

$X_i(X_i(k)|k=1,2,\ldots,6)$ $(i=1,2,\ldots,n); n \geq 2;$    comparative variable wherein the comparative variable $X_i$ represents a set of values of each factor affecting the performance of rubber asphalt as a variable, with i representing the ith component variable and k representing the kth base asphalt;
    tabulating the comparative variables and the reference variable, with different variables being arranged in rows and different samples being arranged in columns;
    performing dimensional normalization: performing dimensional normalization on different variables by dividing each value by an average to obtain respective values of the reference variable and the comparative variables, which are calculated according to Formula (1) below:

$$\begin{cases} Y_0 = \{X_0(k)/\overline{X}_0 \mid k = 1, 2, \ldots 6\} \\ Y_i\{X_i(k)/\overline{X}_i \mid k = 1, 2, \ldots, 6\}(i = 1, 2, \ldots, 6) \end{cases} \quad \text{Formula (1)};$$

where $k = 1, 2, \ldots \ldots, n; n \geq 2$;

$Y_0$ represents a set obtained by dividing each value in $X_0$ by an average of all the values in $X_0$, and $Y_i$ represents a set obtained by dividing each value in $X_i$ by an average of all the values in $X_i$;

calculating differences between sequences: after the dimensional normalization, calculating differences between the values of the reference variable row and each comparative variable row in corresponding columns according to the following Formula (2), and obtaining the absolute values of the differences to form a new table with the reference variable row omitted:

$$\Delta_i(k) = |Y_0(k) - Y_i(k)| \quad \text{Formula (2)};$$

wherein $\Delta_i(k)$ represents the absolute value;

determining grey relational coefficients: calculating relational coefficients of comparative sequences to the reference sequence according to Formula (3) below:

$$\xi_i = \frac{\min_{i=1,n}\left[\min_{k=1,n}\Delta_i(k)\right] + \rho\max_{i=1,n}\left[\max_{k=1,n}\Delta_i(k)\right]}{\Delta_i(k) + \rho\max_{i=1,n}\left[\max_{k=1,n}\Delta_i(k)\right]}; \quad \text{Formula (3)}$$

wherein $\rho$ is an identification coefficient, generally $\rho \in (0, 1)$, having a value of 0.5; and $$\min_i\left[\min_k \Delta_i(k)\right]$$

represents a minimum difference of two extremes, while $$\min_i\left[\min_k \Delta_i(k)\right]$$

represents a maximum difference of two extremes;

calculating grey relational grades according to Formula (4) below:

$$r_i = \frac{1}{n}\sum \xi_i(k); \quad \text{Formula (4)}$$

and calculating respective averages of the relational coefficients to obtain the grey relational grades.

* * * * *